United States Patent [19]

Kamuro et al.

[11] Patent Number: 5,173,106
[45] Date of Patent: Dec. 22, 1992

[54] METHOD FOR INHIBITING FLOWERING OF PLANTS USING S-(+)-ABSCISIC ACID

[76] Inventors: Yasuo Kamuro, 2-15-16, Hanaike, Ichinomiya-shi, Aichi, 491; Shingo Marumo, 3-403, Honjigahara Jutaku, 100-8, Midorigaoka, Midori-cho, Owariasahi-shi, Aichi, 488, both of Japan

[21] Appl. No.: 719,244

[22] Filed: Jun. 24, 1991

[30] Foreign Application Priority Data

Jun. 26, 1990 [JP] Japan .................... 2-167588

[51] Int. Cl.$^5$ .................... A01N 35/06; A01N 37/06
[52] U.S. Cl. .................................. 71/113; 71/123
[58] Field of Search .................................. 71/113

[56] References Cited

FOREIGN PATENT DOCUMENTS 1103000 2/1968 United Kingdom .

OTHER PUBLICATIONS

CA Index Guide, 1985, p. 6G.
Schwabe CA76:136,792m. "Flower Inhibition . . . " (Planta 103: 18-23. 1972). 1972 p. 141.
Kinet et al., CA 84:55,202g. "Inhibition of Flowering by Abscisic Acid . . . " (Z. Pflanzenphysicol. 77:70-74. 1975). 1976 p. 162.
Margara CA 87:63, 991 r. "Effects of Growth Regulators . . . " (C. R. Hebol Search Acad. Sci., Ser D. 284:1991-4. 1977) 1977, p. 182.
Morgan CA 96:29,861z. "Factors affecting fruit . . . " (Monogr. Br. Plant Growth Regul. Group. 1981) 1982 p. 190.
Chem. Abstracts., vol. 104, No. 23, Jun. 9, 1986, p. 451 Abstract No. 203980h, Columbus, Ohio, US.
Chem. Abstracts, vol. 79, No. 15, Oct. 15, 1973, p. 95 Abstract No. 88210h, Columbus, Ohio, US.
Chem. Abstracts, vol. 79, No. 1, Jul. 9, 1973, p. 124, Abstract No. 1257g, Columbus, Ohio, US.
Chem. Abstracts, vol. 73, No. 25, Dec. 21, 1970, p. 278 Abstract No. 129886e, Columbus, Ohio, US.
Biological Abstracts, vol. 73, No. 10, 1982, Abstract No. 71627, Philadelphia, PA, US.
Biological Abstracts, vol. 72, No. 3, 1981, Abstract No. 19916, Philadelphia, PA, US.
Biological Abstracts, vol. 62, No. 10, 1976, Abstract No. 57406, Philadelphia, PA, US.
Agricultural & Biological Chemistry, vol. 54, No. 12, Dec. 1990, pp. 3363-3365, Tokyo, JP.

*Primary Examiner*—Richard L. Raymond
*Assistant Examiner*—S. Mark Clardy

[57] ABSTRACT

A composition for inhibiting flowering of plants and a composition for prolonging the duration of flowering are disclosed. The compositions of the present invention comprise S-(+)-abscisic acid as an effective ingredient.

3 Claims, No Drawings

METHOD FOR INHIBITING FLOWERING OF PLANTS USING S-(+)-ABSCISIC ACID

BACKGROUND OF THE INVENTION

I. Field of the Invention

The present invention relates to a composition for inhibiting flowering of plants and to a composition for prolonging the duration of flowering of plants.

II. Description of the Related Art

Most of the agricultural and horticultural plants form flower buds and then flower depending on the change of season, especially change in the length of the daytime. To inhibit the formation of flower buds or flowering is an important agricultural technique. No technique has been established to completely inhibit the floral bud initiation by using plant hormones. Only one commercially used technique is to inhibit floral bud initiation by artificially controlling the length of the daytime wherein the plants (for example, chrysanthemum) are cultured in an equipment.

However, to artificially control the length of daytime while culturing the plants in an equipment is costly and the scale of the culturing is limited.

Thus, if the floral bud initiation of plants in the fields can be inhibited by applying an agricultural chemical to the plants, it is economical and advantageous.

To attain this object, a number of compounds have been tested for their activities to inhibit the flowering of plants. A number of reports have been published concerning the effectiveness of synthetic racemic abscisic acid for this purpose (Ann. Rev. Plant Physiol. 39, 175 (1988)). However, the results have been negative and no useful technique has been established, which employs synthetic racemic abscisic acid.

SUMMARY OF THE INVENTION

Accordingly, an object of the present invention is to provide a composition and method for inhibiting flowering of plants.

Another object of the present invention is to provide a composition and method for prolonging duration of flowering of plants.

It was surprisingly found by the present inventors that S-(+)-abscisic acid inhibits the flowering of plants and also prolongs the duration of flowering of plants, so that the present invention was completed.

That is, the present invention provides a composition for inhibiting flowering of plants, comprising S-(+)-abscisic acid in an amount effective for inhibiting flowering of plants in an agriculturally acceptable carrier.

The present invention also provides a composition for prolonging duration of flowering of plants, comprising S-(+)-abscisic acid in an amount effective for prolonging duration of flowering of plants in an agriculturally acceptable carrier.

The present invention further provides a method for inhibiting flowering of plants comprising applying effective amount of S-(+)-abscisic acid to said plants before flowering of the plants.

The present invention still further provides a method for prolonging duration of flowering comprising applying effective amount of S-(+)-abscisic acid to said plants before flowering of the plants and after the floral bud initiation.

By the present invention, it was first attained to effectively inhibit the flowering of plants, especially agricultural and horticultural plants, by applying a chemical to the plants. Thus, the present invention will make a great contribution to the agriculture and horticulture. The present invention also provided means for effectively prolonging the duration of flowering, so that flowers can be enjoyed for a longer time than the natural duration of flowering of the plant.

DETAILED DESCRIPTION OF THE PREFERRED EMBODIMENTS

In the present specification and appended claims, the term "inhibit flowering" means to completely inhibit the floral bud initiation or flowering after formation of flower buds, or to delay the floral bud initiation and/or flowering.

As mentioned above, the composition for inhibiting flowering of plants according to the present invention comprises S-(+)-abscisic acid as an effective ingredient in an agriculturally acceptable carrier. S-(+)-abscisic acid is a known compound and may be produced by a conventional method (S. Marumo et al., *Agric. Biol. Chem.*, 46, 1967 (1982); Japanese Laid Open Patent Application (Kokai) Nos. 296697/88 and 296696/88).

The composition of the present invention may be formulated by using one or more conventional agriculturally acceptable carrier. Examples of the agriculturally acceptable carriers which may be employed include solid carriers such as clay, talc, bentonite, kaolin, diatomaceous earth and silica; and liquid carriers such as benzene, xylene, toluene, kerosene, alcohols (methanol, ethanol, isopropanol, n-butanol, ethylene glycol, propylene glycol and the like), ketones (acetone, methylethyl ketone, cyclohexanone and the like) and N-methylpyrrolidone.

The composition of the present invention may be formulated using one or more of the above-mentioned carriers and one or more suitable surfactants, and if desired, other additives such as stabilizers and spreading agents. The composition of the present invention may be in the form of liquid, flowable composition, water-soluble composition (such as tablets, powder and granules), paste or liquid for injection.

To stabilize the composition or to promote the effect of the composition, the composition of the present invention may comprise other agricultural additives such as spreading agents, wetting extenders, dispersing agents, sticking agents and disintegrators.

The composition of the present invention may be applied to the plants directly or after dilution with an appropriate diluent such as water or an organic solvent. The composition of the present invention may be applied to the plants after mixing with other agricultural chemicals such as insecticides, germicides, plant growth regulators and the like.

The composition of the present invention may be applied, for example, by spraying the composition to the leaves and stems of the plants, by drenching the plants with the composition, by pasting the composition on the leaves and stems or by injecting the composition to the roots or stems.

The concentration of S-(+)-abscisic acid in the composition or the diluted composition to be applied to the plants may usually be 0.01 ppm to 1000 ppm. The preferred concentration varies depending on the plant to be treated and on the timing of treatment. In cases where the composition is sprayed onto the plants, the composition may usually be diluted to attain the concentration of S-(+)-abscisic acid of 10–1000 ppm. In cases where the composition is used for drenching the roots or for hydroponic culture, the composition may usually be diluted to attain the concentration of S-(+)-abscisic acid of 0.1 - 50 ppm. In cases where the composition is used as a liquid for injection, the composition may usually be used without dilution, wherein the concentration of the S-(+)-abscisic acid may be 50 to 500 ppm. In cases where the composition is used as a paste, the composition may usually be used also without dilution, wherein the concentration of the S-(+)-abscisic acid may be 0.1 to 10% by weight.

The amount of the composition of the present invention to be applied to the plants varies depending on the plant and the size of the plant, and the suitable amount for a given plant may easily be determine by routine experiments. For example, the amount of the composition of the present invention to be applied to a radish grown in a farm when the composition is sprayed, about 100 liters of the composition may be applied per 10 ares. In cases where the composition of the present invention in the form of liquid for injection is injected to a branch having a thickness of about 1 cm, the composition may usually be used in the amount of about 1-10 ml. In cases where the composition of the present invention in the form of paste is applied to a branch having a thickness of about 1 cm, the composition may usually be used in the amount of about 0.5-5 g.

The composition of the present invention may be applied to the plants one month before the floral bud initiation to before the flowering. In order to completely inhibit the formation of the buds, the composition of the present invention should be applied to the plants before the floral bud initiation.

The composition of the present invention may be used for wide variety of plants. Non-limiting examples of the plants which may be treated with the composition of the present invention may include petalous flowers such as chrysanthemum and rose; vegetables such as spinach, radish, perilla and cabbage; fruits and forest trees such as apple, orange, cryptomeria and cherry.

It was found by the present inventors that S-(+)-abscisic acid not only inhibits the flowering of plants, but also prolongs the duration of flowering. Thus, the present invention also provides a composition for prolonging duration of flowering of plants, comprising S-(+)-abscisic acid in an agriculturally acceptable carrier. The method of formulating the composition, concentration of the S-(+)-abscisic acid in the composition, method of application to the plants and the plants to be treated with the composition are the same as in the composition for inhibiting flowering of plants according to the present invention. The composition for prolonging the duration of the flowering according to the present invention may be applied to the plants before the flowering of the plants and after the floral bud initiation.

The invention will now be described by way of examples thereof. It should be noted that the examples are presented for the illustration purpose only and should not be interpreted in any restrictive way. Unless otherwise specified, all parts and percentage in the examples are by weight.

EXAMPLE 1

Formulation of Liquid Composition

Ten parts of S-(+)-abscisic acid and 90 parts of ethanol were mixed to obtain a liquid composition according to the present invention.

EXAMPLE 2

Formulation of Liquid Composition

Twenty parts of S-(+)-abscisic acid, ten parts of polyethylene glycol monolaurate which is a surfactant, 70 parts of propylene glycol monoethyl ester which is a solvent were mixed to obtain a liquid composition according to the present invention.

EXAMPLE 3

Formulation of Composition in the Form of Paste

Five parts of S-(+)-abscisic acid, 5 parts of ethyl acetate and 95 parts of white vaseline were dissolved at 50° C. and the solvent was removed under vacuum to obtain a composition in the form of paste.

EXAMPLE 4

Formulation of Composition for Injection

In 99.9 parts of 1:1 mixture of water and ethanol, 0.1 part of S-(+)-abscisic acid were dissolved to obtain a composition for injection.

EXAMPLE 5

Effect for Inhibiting Floral Bud Initiation of Japanese Morning Glory (Short-day Plant)

Seeds of Japanese morning glory (*Pharbitis nil*, variety: Violet) were sown in pots with a diameter of 4 cm which contained vermiculite packed therein. The plants were grown in a greenhouse under a long-day regimen with a photoperiod of 16 hours, under which conditions flower buds are not formed. The photoperiod of 16 hours was attained by the aid of an artificial supplemental light source (5000 lux). Five days after germination, dark (short-day) treatment of 15 hours was performed to promote the formation of the flower buds. Five hours before the short-day treatment, the composition prepared in Example 1 was used for drenching the plants after dilution to attain the concentrations of S-(+)-abscisic acid shown in Table 1. Twenty milliliters of the diluted composition was used for the drenching per one pot. Alternatively, five hours before the short-day treatment, the liquid composition prepared in Example 2 was sprayed onto the plants after dilution to attain the concentrations of S-(+)-abscisic acid shown in Table 1. Ten milliliters of the diluted composition was sprayed per 10 young plants. On the next day of the short-day treatment, the plants were transplanted to pots with a diameter of 7 cm containing soil packed therein and were cultivated under a long-day regimen with a photoperiod of 16 hours. Fourteen days after the transplantation, the number of formed flower buds was counted and the average number of flower buds per one plant was calculated.

For comparison, the same experiments as mentioned above were repeated except that the composition used had the same composition as that prepared in Example 1 except that synthetic racemic abscisic acid was used in place of S-(+)-abscisic acid (Comparative Example 1).

The number of flower buds per one plant is shown in Table 1. Each value is the average of 10 plants.

TABLE 1

|  | Effective Ingredient in Liquid | Method of Treatment | Concentration (ppm) | Average Number of Flower Buds/plant |
| --- | --- | --- | --- | --- |
| Control | None | Drench | 0 | 2.6 |
|  |  | Spray | 0 | 2.8 |
| Example 5 | S(+)− | Drench | 1 | 0.8 |
|  |  |  | 5 | 0 |
|  |  |  | 25 | 0 |
|  | Abscisic Acid | Spray | 30 | 1.2 |
|  |  |  | 125 | 0 |
|  |  |  | 500 | 0 |
| Comparative Example 1 | Synthetic Racemic | Drench | 1 | 2.2 |
|  |  |  | 5 | 1.6 |
|  |  |  | 25 | 0.8 |
|  | Abscisic Acid | Spray | 30 | 1.8 |
|  |  |  | 125 | 1.4 |
|  |  |  | 500 | 1.2 |

As shown in Table 1, the floral bud initiation was completely inhibited by using 5 ppm of S-(+)-abscisic acid in case of drenching and 125 ppm of S-(+)-abscisic acid in case of spraying.

In contrast, in Comparative Example 1 in which racemic abscisic acid was used, the floral bud initiation was not completely inhibited either by drenching or spraying.

EXAMPLE 6

Effect for Inhibiting Floral Bud Initiation of Radish and Perilla

Radish (*Raphanus*, variety: Taibyo-soubutori) which is a long-day plant was grown under a long-day regimen with a photoperiod of 16 hours in a greenhouse so as to promote the formation of flower buds. Germinated seeds of radish were kept under a low temperature condition (5° C.) for 20 days before sowing. Perilla (variety: Aojiso) which is a short-day plant was grown under a short-day regimen with a photoperiod of 10 hours in a greenhouse. In either case, pots of 7 cm diameter containing vermiculite were used and each pot carried one plant. The liquid composition prepared in Example 1 was mixed with a liquid fertilizer so as to attain the concentration of S-(+)-abscisic acid of 10 ppm, and the roots of the plants were drenched with the mixture every three days from the cotyledon phase. For comparison, the liquid fertilizer alone was used for the drenching (Comparative Example 2).

The state of growth on 25 days after the start of the treatment are shown in Table 2.

TABLE 2

|  | Test Plant | Repetition of Treatments | State of Growth (Flower Buds Formation) |
| --- | --- | --- | --- |
| Comparative Example 2 | Radish | 0 | Flowering Started |
|  | Perilla | 0 | Flowering Started |
| Example 6 | Radish | 2 | Buds Initiated But Not Flowered |
|  |  | 4 | No Differentiation of Buds Observed |
|  |  | 6 | No Differentiation of Buds Observed |
|  | Perilla | 2 | Buds Were Observed But Not Initiated |
|  |  | 4 | No Differentiation of Buds Observed |
|  |  | 6 | No Differentiation of Buds Observed |

In Comparative Example 2 wherein the plants were not treated with S-(+)-abscisic acid, the plants, either radish and perilla, started to flower after 25 days from the start of the treatment.

In contrast, by treating the plants 4 or 6 times with 10 ppm of S-(+)-abscisic acid every three days after the plants in Comparative Example 2 started to flower, the floral bud initiation was completely inhibited.

EXAMPLE 7

Effect for Delaying Flowering and Prolonging Duration of Flowering of Apple Tree Apple trees of 6-year old planted in pots with a diameter of 30 cm and a depth of 20 cm were treated with the composition of the present invention 10 days before the beginning of the flowering under natural conditions, wherein one tree was planted in one pot. The liquid composition prepared in Example 2 was 200-fold diluted and sprayed such that the plants are uniformly wetted. Alternatively, 10 ml of the composition for injection prepared in Example 4 was injected into the stems of the plants by using an injector driven into the base portions of the stems. The days by which the beginning of the flowering, the full bloom, and the termination of the flowering were delayed than those observed with the non-treated trees are shown in Table 3.

TABLE 3

|  | Method of Treatment | Initiation of Flowering | Full Bloom | Termination of Flowering |
| --- | --- | --- | --- | --- |
| Example 7 | Spray | 3 | 5 | 7 |
|  | Injection | 4 | 10 | 15 |

As shown in Table 3, the timing of the beginning of the flowering, full bloom and the termination of the flowering were delayed in Example 7 than the control. When the flowering ended in the control group, the treated groups were in full bloom. As can be seen from Table 3, the duration of flowering, that is, the duration in which the flowers can be enjoyed was prolonged.

We claim:

1. A method for inhibiting flowering of plants comprising applying 5-25 ppm of (S-(+)-abscisic acid to said plants by drenching before floral bud initiation of said plants.

2. A method for inhibiting flowering plants comprising applying 125-500 ppm of (S-(+)-abscisic acid to said plants by spraying before floral bud initiation of said plants.

3. The method of claim 1, wherein the application of (S-(+)-abscisic acid is repeated 1-6 times.

* * * * *